United States Patent
Tabirian et al.

(10) Patent No.: US 10,274,650 B2
(45) Date of Patent: Apr. 30, 2019

(54) DIFFRACTIVE WAVEPLATE LENSES AND APPLICATIONS

(71) Applicants: Nelson V. Tabirian, Winter Park, FL (US); Svetlana V. Serak, Oviedo, FL (US); David E. Roberts, Apopka, FL (US); Anna Tabirian, Winter Park, FL (US); Diane M. Steeves, Franklin, MA (US); Brian R. Kimball, Shrewsbury, MA (US)

(72) Inventors: Nelson V. Tabirian, Winter Park, FL (US); Svetlana V. Serak, Oviedo, FL (US); David E. Roberts, Apopka, FL (US); Anna Tabirian, Winter Park, FL (US); Diane M. Steeves, Franklin, MA (US); Brian R. Kimball, Shrewsbury, MA (US)

(73) Assignee: Beam Engineering for Advanced Measurements Co., Winter Park, FL (US)

( * ) Notice: Subject to any disclaimer, the term of this patent is extended or adjusted under 35 U.S.C. 154(b) by 256 days.

(21) Appl. No.: 14/688,197

(22) Filed: Apr. 16, 2015

(65) Prior Publication Data
US 2016/0209560 A1    Jul. 21, 2016
US 2018/0120484 A9    May 3, 2018

Related U.S. Application Data

(63) Continuation-in-part of application No. 13/916,627, filed on Jun. 13, 2013, now abandoned, which is a
(Continued)

(51) Int. Cl.
*G02B 5/18*    (2006.01)
*G02C 7/02*    (2006.01)
(Continued)

(52) U.S. Cl.
CPC .......... *G02B 5/1833* (2013.01); *A61F 2/1618* (2013.01); *A61F 2/1654* (2013.01);
(Continued)

(58) Field of Classification Search
CPC .............. G02B 5/1833; G02B 27/4205; G02B 27/4261; G02B 3/0081; G02B 5/001;
(Continued)

(56) References Cited

U.S. PATENT DOCUMENTS 2,435,616 A    2/1948  Vittum
3,721,486 A    3/1973  Bramley
(Continued)

FOREIGN PATENT DOCUMENTS

EP    1970734    9/2008
EP    2088456    12/2009
(Continued)

OTHER PUBLICATIONS

OISE, Optics in the Southeast, Technical Conference and Tabletop Exhibit, Optical Society of America, Orlando, FL., Nov. 12-13, 2003, 9 pages.
(Continued)

*Primary Examiner* — Stephone B Allen
*Assistant Examiner* — Rahman Abdur
(74) *Attorney, Agent, or Firm* — Brian S. Steinberger; Law Offices of Brian S. Steinberger, P.A.

(57) ABSTRACT

Optical lenses, systems, devices and methods for fabricating and manufacturing diffractive waveplate lenses that allow setting the focal length sign of an optical system by positioning the lens with its front or back surface with respect to an incoming circular polarized light beam. Applications for the lenses include optical systems comprising fibers, diode lasers, waveplates, polarizers, and variable lenses, particularly, in the form of a set of polymer films with re-attachable
(Continued)

adhesive layers. And providing a flat mirror with concave or convex function due to diffractive waveplate lens coating.

7 Claims, 10 Drawing Sheets

Related U.S. Application Data continuation of application No. 12/697,083, filed on Jan. 29, 2010, now abandoned.

(60) Provisional application No. 61/980,062, filed on Apr. 16, 2014.

(51) Int. Cl.
| | |
|---|---|
| G02C 7/06 | (2006.01) |
| G02C 7/12 | (2006.01) |
| A61F 2/16 | (2006.01) |
| G02C 7/08 | (2006.01) |
| G02B 5/30 | (2006.01) |
| G02B 27/42 | (2006.01) |
| G02B 5/00 | (2006.01) |
| G02B 6/024 | (2006.01) |
| G02B 6/35 | (2006.01) |
| G02B 3/00 | (2006.01) |
| G02B 3/10 | (2006.01) |
| G02C 7/10 | (2006.01) |

(52) U.S. Cl.
CPC ............ *G02B 3/0081* (2013.01); *G02B 3/10* (2013.01); *G02B 5/001* (2013.01); *G02B 5/1828* (2013.01); *G02B 5/3083* (2013.01); *G02B 6/024* (2013.01); *G02B 6/3534* (2013.01); *G02B 6/3592* (2013.01); *G02B 27/4205* (2013.01); *G02B 27/4211* (2013.01); *G02B 27/4216* (2013.01); *G02B 27/4261* (2013.01); *G02C 7/022* (2013.01); *G02C 7/061* (2013.01); *G02C 7/086* (2013.01); *G02C 7/12* (2013.01); *G02C 7/10* (2013.01); *G02C 2202/16* (2013.01); *G02C 2202/20* (2013.01)

(58) Field of Classification Search
CPC ......................... G02B 27/4216; G02B 5/1828; G02B 5/3083; G02B 6/024; G02B 27/4211; G02B 6/3592; G02B 6/3534; G02B 3/10; G02C 7/086; G02C 7/02; A61F 2/1654; A61F 2/1618
USPC ............ 359/489.01, 489.06, 489.07, 489.15
See application file for complete search history.

(56) References Cited

U.S. PATENT DOCUMENTS

| | | | |
|---|---|---|---|
| 3,897,136 A | 7/1975 | Bryngdahl | |
| 4,160,598 A | 7/1979 | Firester et al. | |
| 4,301,023 A | 11/1981 | Schuberth | |
| 4,698,816 A * | 10/1987 | Chun | G02B 26/06 |
| | | | 359/257 |
| 4,956,141 A | 9/1990 | Allen | |
| 4,983,332 A | 1/1991 | Hahn | |
| 5,032,009 A | 7/1991 | Gibbons | |
| 5,042,950 A | 8/1991 | Salmon, Jr. | |
| 5,047,847 A * | 9/1991 | Toda | A61B 1/05 |
| | | | 348/345 |
| 5,100,231 A | 3/1992 | Sasnett et al. | |
| 5,142,411 A | 8/1992 | Fiala | |
| 5,150,234 A * | 9/1992 | Takahashi | G02B 3/14 |
| | | | 349/1 |
| 5,218,610 A | 6/1993 | Dixon | |
| 5,321,539 A | 6/1994 | Hirabayashi | |
| 5,325,218 A | 6/1994 | Willett | |
| 5,446,596 A | 8/1995 | Mostrorocco | |
| 5,619,325 A * | 4/1997 | Yoshida | G01M 11/3181 |
| | | | 356/491 |
| 5,621,525 A | 4/1997 | Vogeler et al. | |
| 5,712,721 A | 1/1998 | Large | |
| 5,895,422 A | 4/1999 | Hauber | |
| 5,903,330 A | 5/1999 | Funschilling | |
| 5,989,758 A | 11/1999 | Komatsu | |
| 6,091,471 A | 7/2000 | Kim | |
| 6,107,617 A | 8/2000 | Love et al. | |
| 6,139,147 A | 10/2000 | Zhang | |
| 6,170,952 B1 | 1/2001 | La Haye et al. | |
| 6,191,880 B1 | 2/2001 | Schuster | |
| 6,219,185 B1 | 4/2001 | Hyde | |
| 6,320,663 B1 | 11/2001 | Ershov | |
| 6,373,549 B1 | 4/2002 | Tombling et al. | |
| 6,452,145 B1 | 9/2002 | Graves et al. | |
| 6,551,531 B1 | 4/2003 | Ford | |
| 6,678,042 B2 | 1/2004 | Tabirian et al. | |
| 6,728,049 B1 | 4/2004 | Tabirian et al. | |
| 6,792,028 B2 | 9/2004 | Cook | |
| 6,911,637 B1 | 6/2005 | Vorontsov et al. | |
| 7,048,619 B2 | 5/2006 | Park | |
| 7,094,304 B2 | 8/2006 | Nystrom | |
| 7,095,772 B1 | 8/2006 | Delfyett et al. | |
| 7,196,758 B2 | 3/2007 | Crawford | |
| 7,319,566 B2 | 1/2008 | Prince | |
| 7,324,286 B1 | 1/2008 | Glebov | |
| 7,450,213 B2 | 11/2008 | Kim et al. | |
| 7,764,426 B2 | 7/2010 | Lipson | |
| 8,045,130 B2 | 10/2011 | Son | |
| 8,077,388 B2 | 12/2011 | Gerton | |
| 8,264,623 B2 | 9/2012 | Marrucci | |
| 8,520,170 B2 | 8/2013 | Escuti | |
| 8,582,094 B1 | 11/2013 | Shortt | |
| 8,643,822 B2 | 2/2014 | Tan et al. | |
| 8,937,701 B2 | 1/2015 | Rossini | |
| 8,982,313 B2 | 3/2015 | Escuti et al. | |
| 9,541,772 B2 | 1/2017 | De Sio et al. | |
| 9,557,456 B2 | 1/2017 | Tabirian | |
| 9,592,116 B2 | 3/2017 | De Sio et al. | |
| 9,617,205 B2 | 4/2017 | Tabirian | |
| 9,658,512 B2 | 5/2017 | Tabirian | |
| 9,715,048 B2 | 7/2017 | Tabirian et al. | |
| 9,753,193 B2 | 9/2017 | Tabirian et al. | |
| 9,976,911 B1 | 5/2018 | Tabirian et al. | |
| 9,983,479 B2 | 5/2018 | Tabirian et al. | |
| 10,031,424 B2 | 7/2018 | Tabirian et al. | |
| 10,036,886 B2 | 7/2018 | Tabirian et al. | |
| 10,075,625 B2 | 9/2018 | Tabirian et al. | |
| 10,107,945 B2 | 10/2018 | Tabirian et al. | |
| 2001/0002895 A1 | 6/2001 | Kawano | |
| 2001/0018612 A1 | 8/2001 | Carson | |
| 2001/0030720 A1 | 10/2001 | Ichihashi | |
| 2002/0027624 A1 | 3/2002 | Seiberle | |
| 2002/0097361 A1 | 7/2002 | Ham | |
| 2002/0167639 A1 | 11/2002 | Coates | |
| 2003/0021526 A1 | 1/2003 | Bouevitch | |
| 2003/0072896 A1 | 4/2003 | Kwok | |
| 2003/0137620 A1 | 7/2003 | Wang | |
| 2003/0152712 A1 | 8/2003 | Motomura | |
| 2003/0206288 A1 | 11/2003 | Tabirian et al. | |
| 2003/0214700 A1 * | 11/2003 | Sidorin | H01S 5/146 |
| | | | 359/334 |
| 2003/0218801 A1 | 11/2003 | Korniski et al. | |
| 2004/0051846 A1 * | 3/2004 | Blum | G02C 7/049 |
| | | | 351/159.41 |
| 2004/0081392 A1 | 4/2004 | Li | |
| 2004/0105059 A1 | 6/2004 | Ohyama | |
| 2004/0165126 A1 | 8/2004 | Ooi et al. | |
| 2005/0030457 A1 | 2/2005 | Kuan et al. | |
| 2005/0110942 A1 | 5/2005 | Ide | |
| 2005/0219696 A1 | 10/2005 | Albert et al. | |
| 2005/0271325 A1 | 12/2005 | Anderson et al. | |
| 2005/0276537 A1 | 12/2005 | Frisken | |
| 2005/0280717 A1 | 12/2005 | Chen | |

(56) References Cited

U.S. PATENT DOCUMENTS

| | | |
|---|---|---|
| 2006/0008649 A1 | 1/2006 | Shinichiro |
| 2006/0055883 A1 | 3/2006 | Morris |
| 2006/0109532 A1 | 5/2006 | Savas |
| 2006/0221449 A1 | 10/2006 | Glebov et al. |
| 2006/0222783 A1* | 10/2006 | Hayashi ............. C09K 19/3852 428/1.1 |
| 2007/0032866 A1 | 2/2007 | Portney |
| 2007/0040469 A1 | 2/2007 | Yacoubian |
| 2007/0115551 A1 | 5/2007 | Spilman |
| 2007/0122573 A1 | 5/2007 | Yasuike |
| 2007/0132930 A1 | 6/2007 | Ryu et al. |
| 2007/0247586 A1 | 10/2007 | Tabirian |
| 2007/0258677 A1 | 11/2007 | Chigrinov |
| 2008/0226844 A1 | 9/2008 | Shemo |
| 2008/0278675 A1 | 11/2008 | Escuti |
| 2009/0002588 A1 | 1/2009 | Lee et al. |
| 2009/0052838 A1 | 2/2009 | McDowall |
| 2009/0073331 A1 | 3/2009 | Shi |
| 2009/0122402 A1 | 5/2009 | Shemo |
| 2009/0141216 A1 | 6/2009 | Marrucci |
| 2009/0201572 A1 | 8/2009 | Yonak |
| 2009/0256977 A1 | 10/2009 | Haddock |
| 2009/0257106 A1 | 10/2009 | Tan |
| 2009/0264707 A1 | 10/2009 | Hendricks |
| 2010/0003605 A1 | 1/2010 | Gil |
| 2010/0066929 A1 | 3/2010 | Shemo |
| 2011/0069377 A1 | 3/2011 | Wu et al. |
| 2011/0075073 A1 | 3/2011 | Oiwa |
| 2011/0085117 A1 | 4/2011 | Moon et al. |
| 2011/0097557 A1 | 4/2011 | May |
| 2011/0109874 A1 | 5/2011 | Piers |
| 2011/0135850 A1 | 6/2011 | Saha |
| 2011/0188120 A1* | 8/2011 | Tabirian ................. G02B 27/44 359/573 |
| 2011/0234944 A1 | 9/2011 | Powers |
| 2011/0262844 A1 | 10/2011 | Tabirian |
| 2012/0140167 A1 | 6/2012 | Blum |
| 2012/0162433 A1 | 6/2012 | Fuentes Gonzalez |
| 2012/0188467 A1 | 7/2012 | Escuti |
| 2013/0057814 A1 | 3/2013 | Prushinskiy et al. |
| 2013/0202246 A1* | 8/2013 | Meade ..................... G02B 6/30 385/14 |
| 2014/0055740 A1 | 2/2014 | Spaulding |
| 2014/0211145 A1 | 7/2014 | Tabirian |
| 2014/0252666 A1 | 9/2014 | Tabirian |
| 2015/0049487 A1 | 2/2015 | Connor |
| 2015/0081016 A1 | 3/2015 | De Sio et al. |
| 2015/0276997 A1 | 10/2015 | Tabirian et al. |
| 2016/0023993 A1 | 1/2016 | Tabirian |
| 2016/0047955 A1 | 2/2016 | Tabirian et al. |
| 2016/0047956 A1 | 2/2016 | Tabirian et al. |
| 2016/0209560 A1 | 7/2016 | Tabirian et al. |
| 2016/0363484 A1 | 12/2016 | Barak et al. |
| 2016/0363783 A1 | 12/2016 | Blum |
| 2017/0010397 A1 | 1/2017 | Tabirian |

FOREIGN PATENT DOCUMENTS

| | | |
|---|---|---|
| JP | 2001142033 | 5/2001 |
| JP | 2004226752 | 8/2004 |
| UA | 2209751 | 5/1989 |
| WO | 2007122573 | 11/2007 |
| WO | 2008130555 | 10/2008 |
| WO | 2008130559 | 10/2008 |

OTHER PUBLICATIONS

Dierking, Polymer Network-Stabilized Liquid Crystals, Advanced Materials, vol. 12, No. 3, 2000, 15 pages.

Pagliusi et al. Surface-induced photorefractivity in twistable nematics: toward the all-optical control of gain, Opt. Expr. vol. 16, Oct. 2008, 9 pages.

M. Honma, T. Nose, Polarization-independent liquid crystal grating fabricated by microrubbing process, Jpn. J. Appl. Phys., Part 1, vol. 42, 2003, 3 pages.

Anderson, G., et al., Broadband Antihole Photon Sieve Telescope, Applied Optics, vol. 16, No. 18., Jun. 2007, 3 pages.

Early, J. et al., Twenty Meter Space Telescope Based on Diffractive Fresnel Lens, SPIE, U.S. Department of Energy, Lawrence Livermore National Laboratory, Jun. 2003, 11 pages.

Martinez-Cuenca, et al., Reconfigurable Shack-Hartmann Sensor Without Moving Elements,Optical Society of America, vol. 35, No. 9, May 2010, 3 pages.

Serak, S., et al., High-efficiency 1.5 mm Thick Optical Axis Grating and its Use for Laser Beam Combining, Optical Society of America, vol. 32, No., Jan. 2007, 4 pages.

Ono et al., Effects of phase shift between two photoalignment substances on diffration properties in liquid crystalline grating cells, Appl. Opt. vol. 48, Jan. 2009, 7 pgs.

Naydenova et al., "Diffraction form polarization holographic gratings with surface relief in side chain azobenzene polyesters" J. Opt. Soc. Am. B, vol. 15, (1998), 14 pages.

Oh et al., Achromatic polarization gratings as highly efficent thin-film polarizing beamsplitters for broadband light Proc. SPIE vol. 6682, (2007), 4 pages.

Nersisyan, S., et al., Polarization insensitive imaging through polarization gratins, Optics Express, vol. 17, No. 3, Feb. 2, 2009, 14 pages.

Tabirian, et al., PCT Application No. PCT/US15/26186 filed Apr. 16, 2015, Notification of Transmittal of the International Search Report and the Written Opinion of the International Searching Authority dated Jul. 14, 2015, 17 pages.

Tabiryan, et al., The Promise of Diffractive Waveplates, OPN Optics and Photonics News, Mar. 2010, 6 pages.

Tabiryan, et al., Fabricating Vector Vortex Waveplates for Coronagraphy, 2012, 12 pages.

Tabirian, N., et al, U.S. Appl. No. 61/757,259 filed Jan. 28, 2013, 29 pages.

Beam Engineering for Advced Measurements Co., et al., PCT Application No. PCT/US2016/038666 filed Jun. 22, 2016, Notification of Transmittal of the International Search Report and the Written Opinion of the International Searching Authority , or the Declaration dated Oct. 10, 2016, 16 pages.

Nersisyan, et al., Study of azo dye surface command photoalignment material for photonics applications, Applied Optics, vol. 49, No. 10, Apr. 1, 2010, 8 pages.

Nersisyan, et al., Characterization of optically imprinted polarization gratings, Applied Optics, vol. 48, No. 21, Jul. 20, 2009, 6 pages.

Nersisyan, et al., Fabrication of Liquid Crystal Polymer Axial Waveplates for UV-IR Wavelengths, Optics Express, vol. 17, No. 14, Jul. 2009, 9 pages.

Nersisyan, et al., Optical Axis Gratings in Liquid Crystals and Their Use for Polarization Insensitive Optical Switching, Journal of Nonlinear Optical Physics & Materials, vol. 18, No. 1, 2009, 47 pages.

Nersisyan, et al., Polarization insensitive imaging through polarization gratings, Optics Express, vol. 17, No. 3, Feb. 2, 2009, 14 pages.

Sarkissian, et al., Longitudinally modulated nematic bandgap structure, Optical Society of America, vol. 23, No. 8, Aug. 2008, 6 pages.

Sarkissian, et al., Polarization-universal bandgap in periodically twisted nematics, Optics Letters, vol. 31, No. 11, Jun. 1, 2006, abstract, 4 pages.

Sarkissian, et al., Periodically Aligned Liquid Crystal: Potential Application for Projection Displays, Mol. Cryst. Liq. Cryst., vol. 451, 2006, 19 pages.

Sarkissian, et al., Potential application of Periodically Aligned Liquid Crystal cell for projection displays, JThE12, 2005, 3 pages.

Sarkissian, et al., Polarization-Controlled Switching Between Diffraction Orders in Transverse-Periodically Aligned Nematic Liquid Crystals, Optics Letters, Aug. 2006, abstract, 4 pages.

Schadt, et al., Photo-Induced Alignment and Patterning of Hybrid Liquid Crystalline Polymer Films on Single Substrates, Jpn. J. Appl. Phys., vol. 34, Part 2, No. 6B, Jun. 15, 1995, 4 pages.

Schadt , et al., Photo-Generation of Linearly Polymerized Liquid Crystal Aligning Layers Comprising Novel, Integrated Optically

(56) References Cited

OTHER PUBLICATIONS

Patterned Retarders and Color Filters, Jpn. J. Appl. Phys., vol. 34, Part 1, No. 6A, Jun. 1995, 10 pages.
Schadt, et al., Optical patterning of multi-domain liquid-crystal displays with wide viewing angles, Nature, vol. 381, May 16, 1996, 4 pages.
Escuti, et al., A Polarization-Independent Liquid Crystal Saptial-Light-Modulator, Liquid Crystals X, Proc. of SPIE, vol. 6332, 2006, 9 pages.
Escuti, et al., Polarization-Independent LC Microdisplays Using Liquid Crystal Polarization Gratings: A Viable Solution (?), Dept of Electrical & Computer Engineering @ ILCC, Jul. 1, 2008, 30 pages.
Escuti, et al., Simplified Spectropolarimetry Using Reactive Mesogen Polarization Gratings, Imaging Spectrometry XI, Proc. of SPIE, vol. 6302, 2006, 11 pages.
Gibbons, et al., Surface-mediated alignment of nematic liquid crystals with polarized laser light, Nature, vol. 351, May 2, 1991, 1 page.
Gibbons, et al., Optically Controlled Alignment of Liquid Crystals: Devices and Applications, Molecular Crystals and Liquid Crystals, vol. 251, 1994, 19 pages.
Gibbons, et al., Optically generated liquid crystal gratings, Appl. Phys. Lett., 65, Nov. 14, 1994, 3 pages.
University of Central Florida, School of Optics CREOL PPCE, Optics in the Southeast, Technical Conference and Tabletop Exhibit, Nov. 12-13, 2003, 9 pages.
Ichimura, et al., Surface assisted photoalignment control of lyotropic liquid crystals, Part 1, Characterization and photoalignment of aqueous solutions of a water soluble dyes as lyotropic liquid crystals, J. Materials. Chem., vol. 12, 2002, abstract, 2 pages.
Ichimura, et al., Reversible Change in Alignment Mode of Nematic Liquid Crystals Regulated Photochemically by "Command Surfaces" Modified with an Azobenzene Monolayer, American Chemical Society, Langmuir, vol. 4, No. 5, 1988, 3 pages.
Zel'Dovich, et al., Devices for displaying visual information, Disclosure, School of Optics/CREOL, University of Central Florida, Jul. 2000, 10 pages.
Provenzano, et al., Highly efficient liquid crystal based diffraction grating induced by polarization holograms at the aligning surfaces, Applied Physics Letter 89, 2006, 4 pages.
Titus, et al., Efficient polarization-independent, re ective liquid crystal phase grating, Applied Physics Letter 71, Oct. 20, 1197, 3 pages.
Chen, et al. An Electrooptically Controlled Liquid-Crystal Diffraction Grating, Applied Physics Letter 67, Oct. 30, 1995, 4 pages.
Kim, et al., Unusual Characteristics of Diffraction Gratings in a Liquid Crystal Cell, Advanced Materials, vol. 14, No. 13-14, Jul. 4, 2002, 7 pages.
Pan, et al., Surface Topography and Alignment Effects in UV-Modified Polyimide Films with Micron Size Patterns, Chinese Journal of Physics, vol. 41, No. 2, Apr. 2003, 8 pages.
Fuh, et al., Dynamic studies of holographic gratings in dye-doped liquid-crystal films, Optics Letter, vol. 26, No. 22, Nov. 15, 2001, 3 pages.
Yu, et al., Polarization Grating of Photoaligned Liquid Crystals with Oppositely Twisted Domain Structures, Molecular Crystals Liquid Crystals, vol. 433, 2005, 7 pages.
Crawford, et al., Liquid-crystal diffraction gratings using polarization holography alignment techniques, Journal of Applied Physics 98, 2005, 10 pages.
Seiberle, et al., 38.1 Invited Paper: Photo-Aligned Anisotropic Optical Thin Films, SID 03 Digest, 2003, 4 pages.
Wen, et al., Nematic liquid-crystal polarization gratings by modification of surface alignment, Applied Optics, vol. 41, No. 7, Mar. 1, 2002, 5 pages.
Anagnostis, et al., Replication produces holographic optics in volume, Laser Focus World, vol. 36, Issue 3, Mar. 1, 2000, 6 pages.
Gale, Replicated Diffractive Optics and Micro-Optics, Optics and Photonics News, Aug. 2003, 6 pages.
McEldowney, et al., Creating vortex retarders using photoaligned LC polymers, Optics Letter, vol. 33, No. 2, Jan. 15, 2008, 3 pages.
Marrucci, et al., Pancharatnam-Berry phase optical elements for wave front shaping in the visible domain, Appl. Phys. Lett. 88, 2006, 3 pages.
Stalder, et al., Lineraly polarized light with axial symmetry generated by liquid-crystal polarization converters, Optics Letters vol. 21, No., 1996, 3 pages.
Kakichashvili, et al., Method for phase polarization recording of holograms, Sov. J. Quantum. Electron, vol. 4, No. 6, Dec. 1974, 5 pages.
Todorov, et al., High-Sensitivity Material With Reversible Photo-Induced Anisotropy, Optics Communications, vol. 47, No. 2, Aug. 15, 1983, 4 pages.
Attia, et al., Anisoptropic Gratings Recorded From Two Circularly Polarized Coherent Waves, Optics Communications, vol. 47, No. 2, Aug. 15, 1983, 6 pages.
Cipparrone, et al., Permanent polarization gratings in photosensitive langmuir blodget films, Applied Physics Letter, vol. 77, No. 14, Oct. 2, 2000, 4 pages.
Nikolova, et al., Diffraction Efficiency and Selectivity of Polarization Holographic Recording, Optica Acta: International Journal of Optics, vol. 31, No. 5, 1984, 11 pages.
Lee et al., "Generation of pretilt angles of liquid crystals on cinnamte-based photoalignment . . . ", Opt., Expr., vol. 17 (26) (Dec. 2009), abstract, 4 pages.
Yaroshchuk et al. "Azodyes as photoalignment agents for polymerizable liquid crystals", IDW'06 Digest vol. 1-3, 2006, 4 pages.
Chigrinov et al. "Anchoring properties of photoaligned azo-dye materials" Phys. Rev., E vol. 68, (Dec. 2003), 5 pages.
Tabiryan, et al., Broadband waveplate lenses, Optics Express 7091, vol. 24, No. 7, Mar. 24, 2016, 12 pages.
Tabiryan, et al. Thin waveplate lenses of switchable focal length—new generation in optics, Optics Express 25783, vol. 23, No. 20, Sep. 19, 2015, 12 pages.
Tabiryan, et al. Superlens in the skies: liquid-crystal-polymer technology for telescopes, Newsroom, 2016, 2 pages.
Nersisyan, et al., The principles of laser beam control with polarization gratings introduced as diffractive waveplates, Proc. of SPIE, vol. 7775, 2010, 10 pages.
Heller, A Giant Leap for Space Telescopes, Foldable Optics, S&TR, Mar. 2003, 7 pages.
Beam Engineering for Advanced Measurements Co., PCT Application No. PCT/US2015026186, The Extended European Search Report, dated Mar. 8, 2017, 13 pages.
Blinov, et al., Electrooptic Effects in Liquid Crystal MAterials, Springer-Verlag New York, 1994, 17 pages.
Crawford, et al., Liquid Crystals in Complex Geometries; Formed by Polymer and Porous Networks, Taylor and Francis, 1996, 4 pages.
Honma, et al., Liquid-Crystal Fresnel Zone Plate Fabricated by Microrubbing, Japanese Journal of Applied Phsyics, vol. 44, No. 1A, 2005, 4 pages.
Sobolewska et al., "On the inscription of period and half period surface relief gratings in azobenzene-functionalized polymers", J. Phys. Chem., vol. 112 (15) Jan. 3, 2008, 10 pages.
Barrett et al., Model of laser driven mass transport in thin films of dye-functionalized polymers, J. Chem. Phys., vol. 109 (4), Jul. 22, 1998, 13 pages.
Tabirian, U.S. Appl. No. 14/214,375, filed Mar. 14, 2014, Office Action Summary dated Jun. 27, 2017, 10 pages.
Tabirian, et al., U.S. Appl. No. 14/688,425, filed Apr. 16, 2015, Office Action Summary dated Oct. 5, 2017, 10 pages.
Serak, et al. Diffractive Waveplate Arrays [Invited], Journal of the Optical Society of America B, May 2017, pp. B56-B63, vol. 34, No. 5, 8 pages.
Emoto, et al., Optical and Physical Applications of Photocontrollable Materials: Azobenzene-Containing and Liquid Crystalline Polymers, Polymers, Jan. 2012, 150-186, vol. 4, 38 pages.
Pepper, M. et al, Nonlinear Optical Phase Conjugation, IEEE, Sep. 1991, pp. 21-34, 14 pages.
Tabirian, N., Utility U.S. Appl. No. 14/194,808, filed Mar. 2, 2014, Office Action Summary dated Feb. 9, 2018, 10 pages.

(56) References Cited

OTHER PUBLICATIONS

Tabirian, N., Utility U.S. Appl. No. 14/324,126, filed Jul. 4, 2014, Office Action Summary dated Feb. 8, 2018, 13 pages.
De Sio, L., et al., "Digital Polarization Holography Advancing Geometrical Phase Optics," 2016, Optics Express, vol. 24, Issue 16, pp. 18297-18306, 10 pages.
Borek, G. and D. Brown, "High-performance diffractive optics for beam shaping," 1999, Proceeding of SPIE, vol. 3633, pp. 51-60, 10 pages.
Gerchberg, et al, practical algorithm for the determination of the phase from image and diffraction plane pictures, 1972, Optik, vol. 35, Issue 2, pp. 237-246, 10 pages.
Tabirian, N., Utility U.S. Appl. No. 15/189,551, filed Jun. 22, 2016, Office Action Summary dated Feb. 27, 2018, 16 pages.
Tabirian, et al., Utility U.S. Appl. No. 14/688,197, filed Apr. 16, 2015, Office Action Summary dated Aug. 6, 2018, 19 pages.

\* cited by examiner

DIFFRACTIVE WAVEPLATE LENSES AND APPLICATIONS

CROSS REFERENCE TO RELATED APPLICATIONS

This application claims the benefit of priority to U.S. Provisional Application Ser. 61/980,062 filed Apr. 16, 2014, the entire application of which is incorporated by reference in its' entirety, and this application is a Continuation-In-Part of U.S. patent application Ser. No. 13/916,627 filed Jun. 13, 2013, now abandoned, which is a Continuation of U.S. patent application Ser. No. 12/697,083 filed Jan. 29, 2010, now abandoned.

GOVERNMENT LICENSE RIGHTS

This invention was made in part with U.S. Government support under Army Contract No. W911QY-12-C-0016. The government has certain rights in this invention.

FIELD OF INVENTION

This invention relates to optical lenses, and in particular to systems, devices, and methods of fabricating and manufacturing optical lenses used for imaging optics and systems, astronomy, displays, polarizers, optical communication and other areas of laser and photonics technology.

BACKGROUND OF THE INVENTION

The present invention is in the technical field of optics. More particularly, the present invention is in the technical field of lenses, systems of lenses, imaging and controlling of light beams. Lenses are commonly made by shaping an optical material such as glass. The weight of such lenses increases strongly with diameter making them expensive and prohibitively heavy for applications requiring large area. Also the quality of a lens typically decreases with increasing size. To achieve desirable features such as high-quality imaging, conventional lenses sometimes have curved surfaces that are non-spherical. The need to grind and polish conventional lenses with non-spherical surfaces can make such lenses extremely expensive. Segmented lenses such as Fresnel lenses are relatively thin, however, the structural discontinuities result in severe aberrations. Uses of holographic lenses are limited by the compromise of efficiency, spectral bandwidth and dispersion. Thus, there is a need for lenses that could be obtained in the form of thin film structurally continuous coatings on a variety of substrates for a variety of spectral ranges.

Thus, the need exists for solutions to the above problems with the prior art.

SUMMARY OF THE INVENTION

A primary objective of the present invention is to provide systems, devices, and methods for providing a structurally continuous thin film lens wherein the sign of its focal length can be chosen to be positive or negative by flipping the lens.

The second objective of the present invention is providing an imaging system comprising a DW lens with spherically or cylindrically symmetric continuous structure, deposited on a variety of substrate such as optical fiber facet, a refractive lens, a birefringent lens, a phase retardation plate or a tunable lens.

The third objective of the present invention is providing sunglasses, swimming goggles, and goggles for eye protection that employ continuous thin film structures, that correct for human vision defects as do conventional prescription sunglasses or goggles but that perform this function without requiring curved lens surfaces.

The fourth objective of the present invention is providing a lens with continuous thin film structure whose properties can be changed in a useful way by application of an electrical potential to the lens.

The fifth objective of the present invention is providing a lens with a continuous thin film structure on a non-planar surface.

The sixth objective of the present invention is providing a flat mirror coated with a continuous thin film structure that focuses or defocuses light.

Further objects and advantages of this invention will be apparent from the following detailed description of the presently preferred embodiments which are illustrated schematically in the accompanying drawings.

DETAILED DESCRIPTION OF THE INVENTION

Figure 1A:
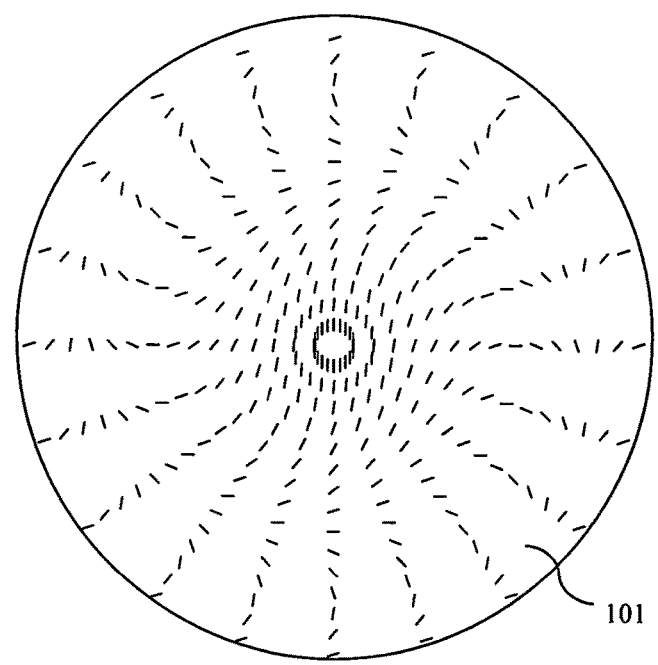
FIG. 1A shows spatial distribution of optical axis orientation in spherical diffractive waveplate lenses of one sign.

Before explaining the disclosed embodiments of the present invention in detail it is to be understood that the invention is not limited in its applications to the details of the particular arrangements shown since the invention is capable of other embodiments. Also, the terminology used herein is for the purpose of description and not of limitation.

In the Summary above and in the Detailed Description of Preferred Embodiments and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, that feature can also be used, to the extent possible, in combination with and/or in the context of other particular aspects and embodiments of the invention, and in the invention generally.

In this section, some embodiments of the invention will be described more fully with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will convey the scope of the invention to those skilled in the art. Like numbers refer to like elements throughout, and prime notation is used to indicate similar elements in alternative embodiments.

A list of components will now be described.
101 left hand thin film
102 right hand thin film
201 continuous lines
301 observer
302 observer
400 component/element
410 right-hand circular polarized (RHCP) light beam
411 defocused RHCP light beam
412 focused RHCP light beam
420 left-hand circular polarized (LHCP) light beam
421 defocused (LHCP) light beam
422 focused LHCP beam
430 DWL layer
440 substrate
610 one-hand circular polarized light
612 focused light
620 opposite-hand circular polarized light
621 defocused light
630 DWL layer
640 substrate
650 aperture
660 circular polarizer
701 sunglasses
702 quarter wave phase retardation plate
703 DML film
801 DW lenses
802 functional layers
803 adhesive backing
804 support sheet
900 refractive lens
901 adhesive
902 DWL
1001 circular polarized collimated light beam
1002 DWL
1003 quarter waveplate
1004 flat mirror
1005 focused beam Glossary of Terms:
Diffractive waveplate (DWs): A birefringent film with anisotropy axis orientation modulated in the plane of the film. Different modulation patterns are possible resulting in different optical functionality, including lens, prism, axicon, etc. Generally, DWs may possess more than one layer, and the anisotropy axis may be modulated also in the bulk of the layer.
Diffractive waveplate lens: A diffractive waveplate with lens function. It may provide spherical, cylindrical, and other types of lens action.
Optical substrate or optical film: A transparent material providing mechanical support for DWs. It may be glass, quartz, plastic, or any other material that is at least partially transparent for the wavelengths of light that propagate through the DWs. It may possess anti-reflective or anti-scratch functions.
Switchable Diffractive waveplate: A DW that can be switched between diffractive and non-diffractive states upon application of external influences such as electric fields, temperature, optical radiation, etc. Generally, the switching can take place through gradual change of diffraction spectrum.
Variable phase retarder or polarization controller: An optical component capable of controlling the polarization of light propagated through it by applying electric fields, changing temperature, exposure to a light beam, etc. Particularly, it may be a liquid crystal sandwiched between substrates coated with transparent electrodes.

In the following description of the invention, the term "light" will often be used to describe the electromagnetic radiation that interacts with the diffractive waveplate lenses that are the subject of this invention. Although "light" generally means electromagnetic radiation with a wavelength in the visible region of the electromagnetic spectrum, it should be understood that the usage of the term "light" in the description is not restrictive, in the sense of limiting the design and application to diffractive waveplate lenses that operate only in the visible region of the spectrum. In general, all the designs and concepts described herein apply to operation over a wide range of the electromagnetic spectrum, including the microwave, infrared, visible, ultraviolet, and X-ray regions. While physical embodiments of diffractive waveplate lenses are at present advanced for operation in the visible region of the spectrum, the designs and applications disclosed here are applicable over all the noted regions of the electromagnetic spectrum.

Many of the exemplary applications have been described herein with terms such as "light" being used to describe the electromagnetic radiation that is acted upon by the disclosed diffractive waveplate lenses. The term "light" in this context should not be taken to restrict the scope of the disclosed embodiments to only those in which the electromagnetic radiation acted upon or manipulated by the diffractive waveplate lenses is in the visible region of the spectrum. As will be evident to those skilled in the art, the exemplary embodiments disclosed here, in addition to being applicable in the visible region of the spectrum, are equally applicable to the microwave, infrared, ultraviolet, and X-ray regions of the spectrum. Exceptions to this generalization are the applications relating to human vision, for which operation in the visible region of the spectrum is required.

The present invention relates to the design and application of diffractive waveplate lenses. The term "diffractive waveplate lens" as used herein describes a thin film of birefringent material deposited on a transparent structure, for example, a thin flat substrate of optical material such as glass. This birefringent film has the property that it retards the phase of light of one linear polarization by approximately one half wave (pi radians of optical phase) relative to the light of the other linear polarization. In diffractive waveplate lenses, the optical axis orientation depends on the transverse position on the waveplate, i.e. the position in the two coordinate axes perpendicular to the surface of the diffractive waveplate lens. In other words, the optical axis orientation is modulated in one or both of the transverse directions parallel to the surface of the substrate on which the active thin film is applied. Lensing action is due to parabolic profile of optical axis orientation modulation.

There are two general types of diffractive waveplate lenses to which the present invention applies. The first type of diffractive waveplate lens is axially symmetric and is used, for example, to focus a collimated beam of light to a point in space. The second type of diffractive waveplate lens is cylindrically symmetric and is used, for example, to focus a collimated beam of light to a line segment in space. In many examples below, an optical system of circular symmetry is used as an example, but in general, all of the conclusions apply as well to optical systems of cylindrical symmetry.

Lenses that Allow Choosing the Sign of the Focal Length Depending on Orientation In FIG. 1, the orientation of the anisotropy axis at each point of the birefringent thin film 101 is indicated by a short line segment. In the first type of diffractive waveplate lenses to which the present invention applies, illustrated in FIG. 1A, the orientation of the anisotropy axis of the birefringent material including the thin film layer depends only on the radial distance r from a center point. This type of spherical diffractive waveplate lens is used for applications such as focusing a collimated beam of light to a point for imaging a distant scene onto a sensor array. To perform this function, the angle α that the anisotropy axis of the birefringent material makes with the coordinate axis is given by the following equation:

$$\alpha = \pm \frac{k_0}{4f} r^2$$

where $k_0=2\pi/\lambda$ is the wavenumber of the light that is to be focused by the diffractive waveplate lens, λ is the wavelength of that radiation, f is the focal length of the diffractive waveplate lens (DWL), and r is the distance to the central point.

Figure 1B:
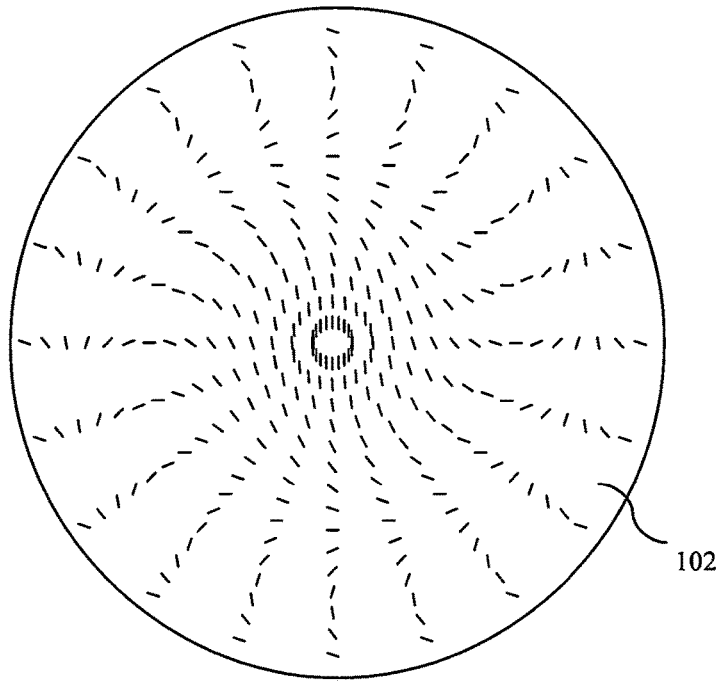
FIG. 1B shows spatial distribution of optical axis orientation in spherical diffractive waveplate lenses of an opposite sign.
Figure 2A:
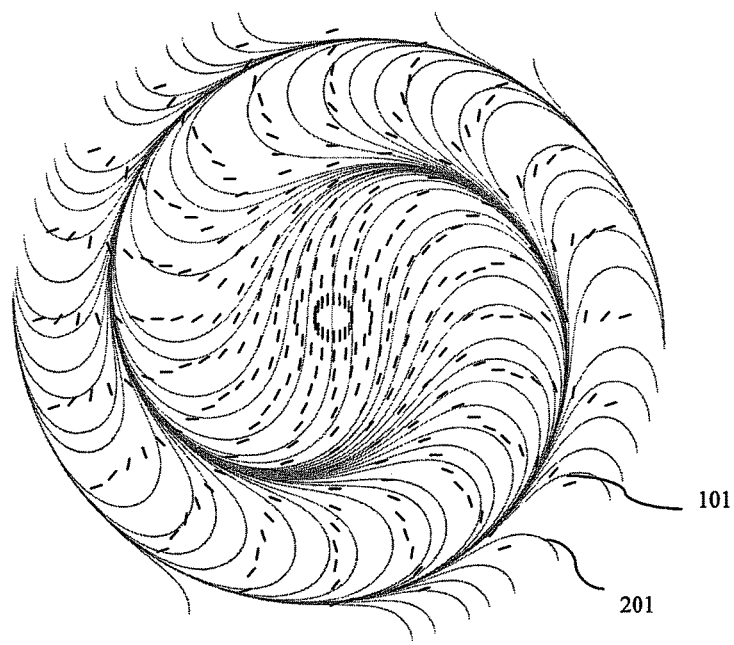
FIG. 2A shows a representation of a spherical diffractive waveplate lens with continuous alignment lines of anisotropy axis of the birefringent material.
Figure 2B:
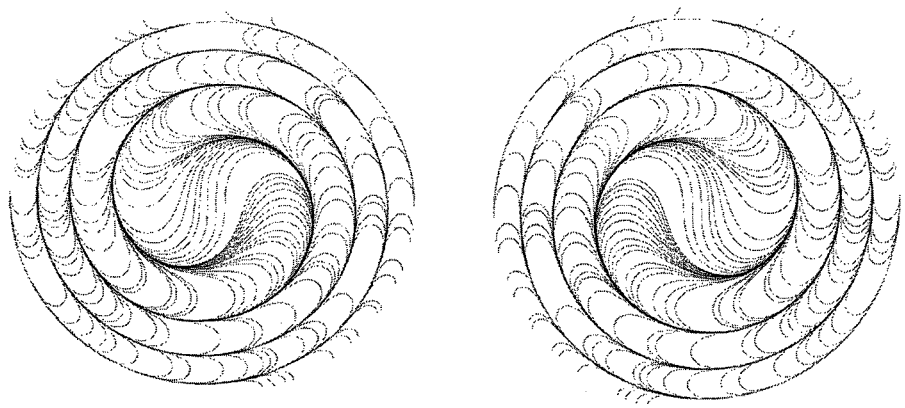
FIG. 2B shows spherical diffractive waveplate lenses of opposite signs in description with continuous alignment lines.

The difference in signs in variation of the anisotropy axis with radius designate lenses of two opposite signs. The difference in corresponding patterns 101 and 102 in FIGS. 1A and 1B is even better visible in representation of the DWL structure by continuous lines 201 as shown in FIG. 2A. DWLs of different signs correspond to the right- and left-spiraling patterns shown in FIG. 2B, respectively.

Figure 3:
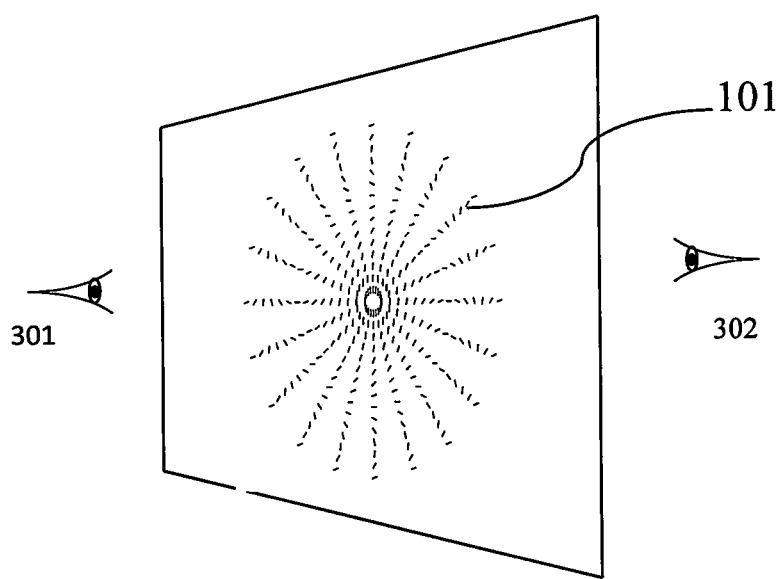
FIG. 3 shows a diffractive waveplate lense viewed from opposite sides.

In the preferred embodiment of the present invention, DWLs of opposite optical axis modulation signs need not be two separate optical components and is obtained by rotating the DWL around an axis in the plane of the DWL by 180 degrees. The observers 301 and 302 looking at a given DWL from opposite sides as shown in FIG. 3 see patterns of opposite sign.

Figure 4A:
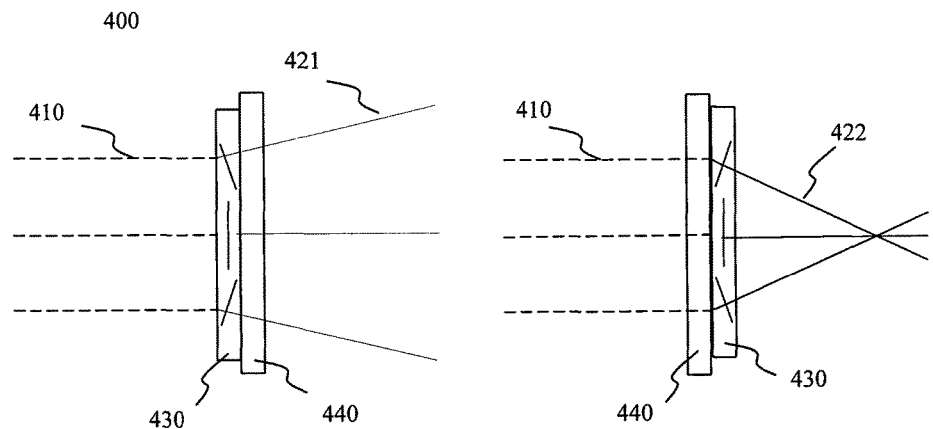
FIG. 4A shows polarization properties of focusing and defocusing of a right-hand circular polarized beam by a diffractive waveplate lens, respectively.

This optical asymmetry is described in detail in regard to FIG. 4A wherein the DWL layer 430 is shown on a substrate 440. As an example, a right-hand circular polarized (RHCP) light beam 410 is transformed into a defocused left-hand circular polarized (LHCP) beam 421 when incident from the side of the substrate. Arranging the component 400 with the substrate facing the incident RHCP beam results in a focused LHCP beam 422.

Figure 4B:
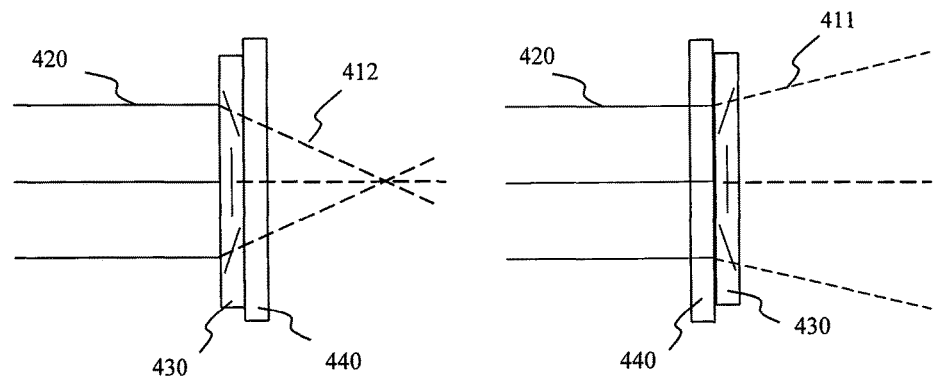
FIG. 4B shows polarization properties of focusing and defocusing a left-hand circular polarized beam by a diffractive waveplate lens, respectively.

For a LHCP light beam 420 in FIG. 4B, the situation is reversed. The LHCP beam 420 is transformed into a focused RHCP beam 412 when incident from the side of the DWL and it is transformed into defocused RHCP beam 411 when incident from the side of the substrate.

Cylindrical DWL

Figure 5A:
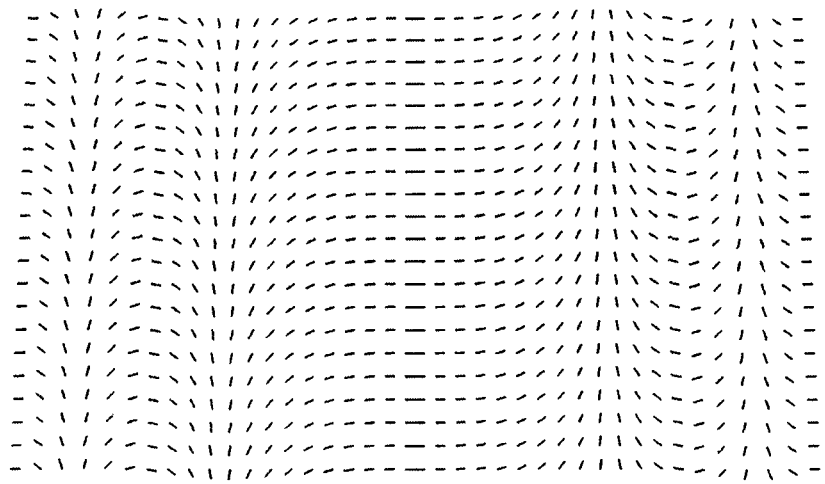
FIG. 5A shows the structure of a cylindrical diffractive waveplate lens.
Figure 5B:
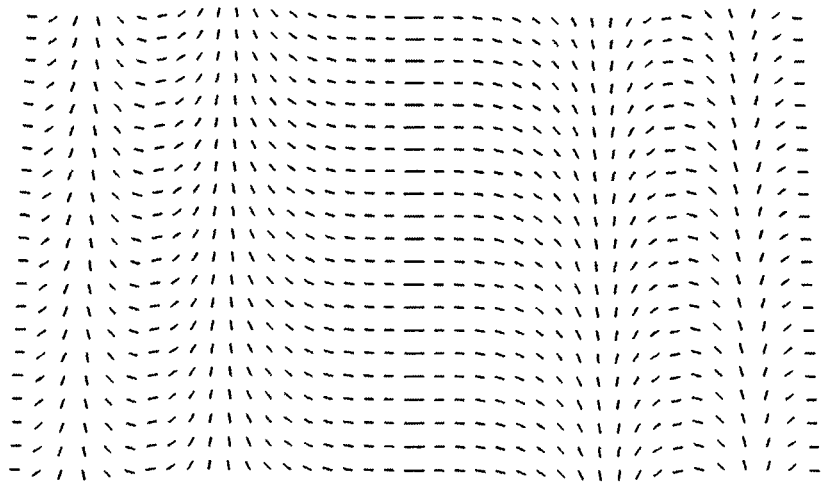
FIG. 5B shows the structure of another cylindrical diffractive waveplate lens.

In the second type of diffractive waveplate lenses to which the present invention applies, illustrated in FIGS. 5A and 5B, the orientation of the optical axis of the birefringent material of the thin film layer depends only on the linear distance x from a central axis. This type of cylindrical diffractive waveplate lens is used for applications such as focusing a beam of light to a line for imaging light from the sun onto a line of photovoltaic devices. In the paraxial approximation, the angle α that the optical axis of the birefringent material makes with the coordinate axis is given by the following equation:

$$\alpha = \pm \frac{k_0}{4f} x^2$$

where $k_0$ and f have the same meanings as before, and x is the distance from the center of the coordinate axis. FIGS. 5A and B correspond to patterns of different sign (cylindrical lenses of different sign).

Operation for Unpolarized Light

Figure 6A:
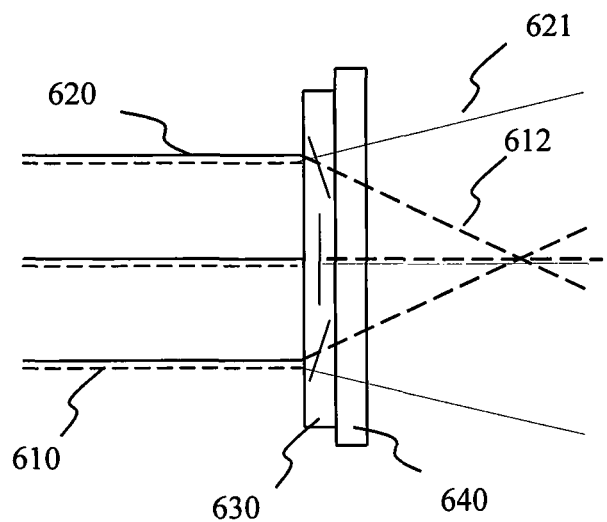
FIG. 6A shows the presence of both focused and defocused beams when an unpolarized light is incident on a diffractive waveplate lens.
Figure 6B:
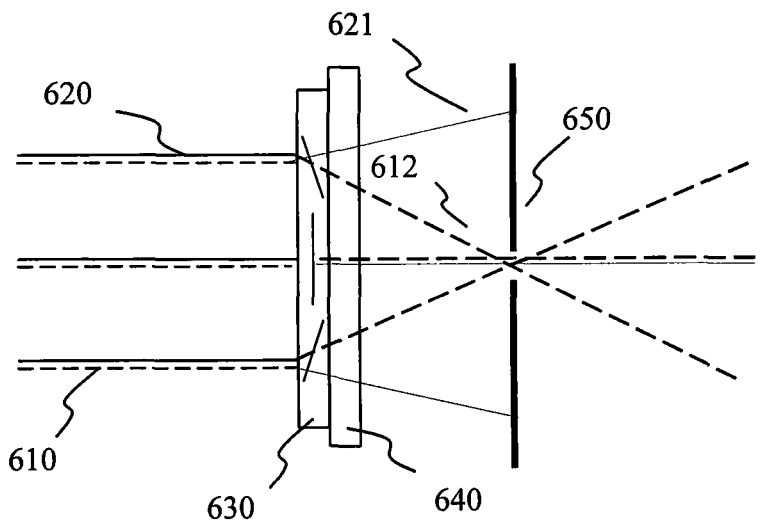
FIG. 6B shows a method for spatially filtering out the defocused beam.
Figure 6C:
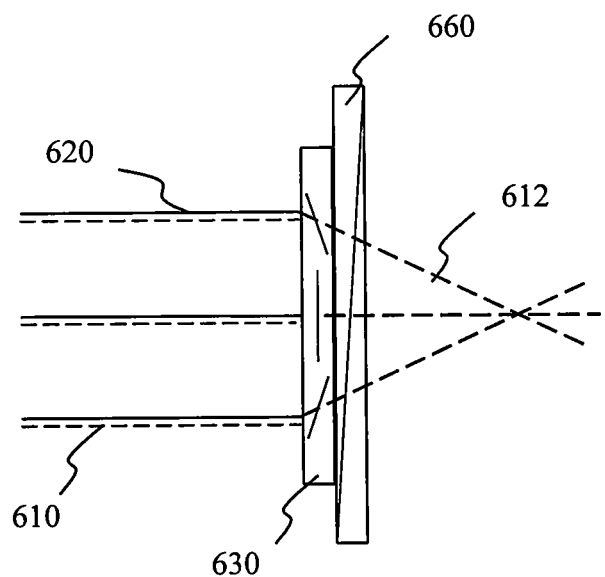
FIG. 6C shows the method for filtering out the defocused beam by a circular polarizer.

In many imaging applications, the source of light is unpolarized. In such a case show in FIG. 6A the DWL focuses one hand of circular polarized component of light 620 and defocuses the opposite one 610. The power density of the defocused light 621 decreases rapidly with propagation distance and can still allow imaging for the focused portion of the light 612. An aperture 650 can be introduced in the system as shown in FIG. 6B to allow propagation of the focused component while further attenuating the defocused beam propagated through the system and to the sensor. The defocused polarization can be fully blocked using a circular polarizer 660 as shown in FIG. 6C. In realization show in FIG. 6C, the polarizer film is integrated with the DWL and can serve as a substrate.

Figure 7:
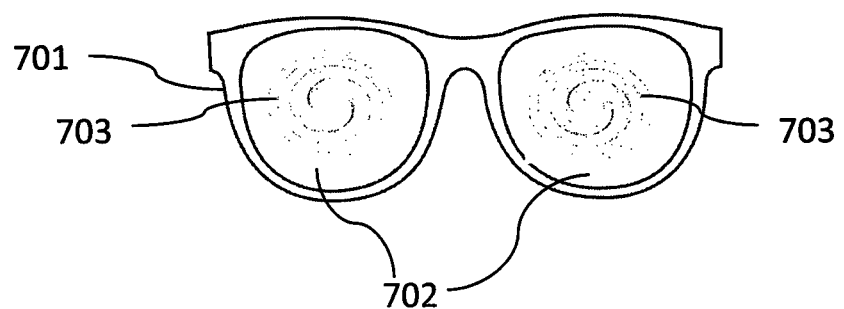
FIG. 7 shows glasses having diffractive waveplate lens coatings.

In a particularly important application, polarized sunglasses, goggles, etc. can serve as such a substrate. Attaching DWL films 703 on circular polarizing glasses 702 may impart ophthalmic action on sunglasses, protective goggles, ski goggles, and other protective eye ware shown as 701 in FIG. 7. Further, a quarter wave phase retardation plate can be integrated with the DWL to be used with sunglasses that are linearly polarized.

An example of uses of electrically switchable diffractive waveplate lenses of the present invention are camera lenses and machine vision wherein the contrast reduction due to presence of defocused beam does not affect required image information obtained due to focused portion of the beam.

Combination with Other Functional Layers

Figure 8:
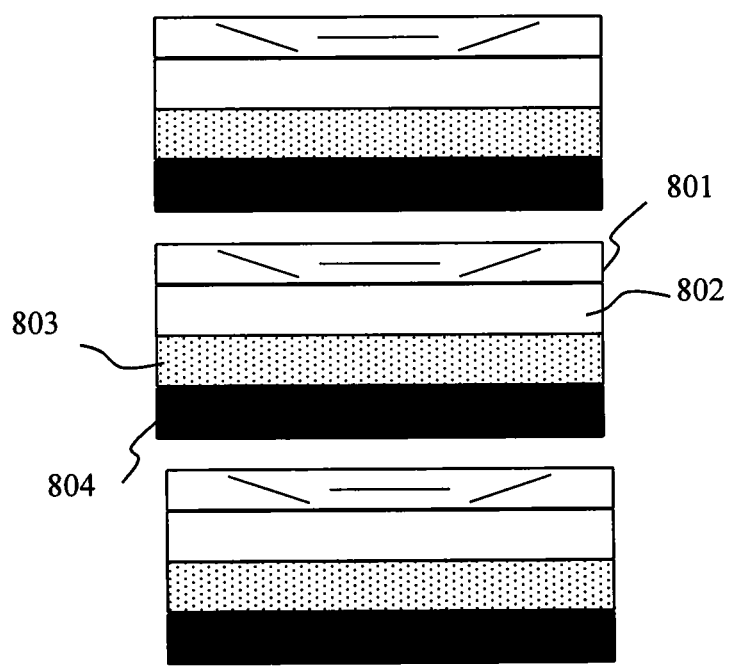
FIG. 8 shows a kit comprising diffractive waveplate lenses with reattachable adhesive backing.
Figure 9:
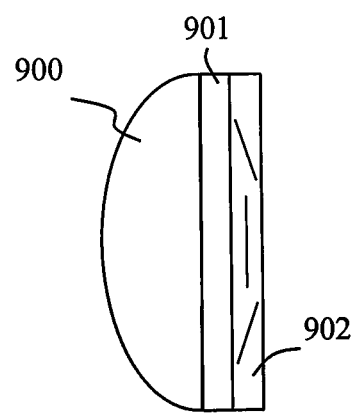
FIG. 9 shows application of a diffractive waveplate lens on a refractive lens.

The DW lenses 801 shown in FIG. 8, along with other functional layers 802, may have an adhesive backing 803 for attachment to a support sheet 804 making up a kit that incorporates many DWLs that could be detached and reattached to a different substrate such as a refractive lens. This is demonstrated in FIG. 9 where 900 is a refractive lens, 901 is the adhesive, and 902 designates DWL with all other functional layers as required for different applications. The refractive lens can be birefringent and/or variable.

Vision Correction

The flexibility of being able to change the properties of a diffractive waveplate lens simply by changing the pattern of the optical axis orientation in the thin film of the lens does not apply only to correcting for spherical aberrations, it applies to the other types of imaging aberrations well known in the art of optical design. Additionally, the present invention provides the opportunity of fabricating bifocal ophtalmic lenses by smooth variations of the orientation pattern in the thin film diffractive waveplate. In one embodiment of the current invention for ophthalmic uses, the flexibility of producing any desired orientation pattern can be used to inexpensively fabricate lenses fine-tuned to precisely correct eye aberrations.

A very common application of optical systems is to correct for deficiencies in human vision. In this application, in common eyeglasses, a refractive lens is placed in front of each eye. The corrective optical element is fabricated from a refractive medium, such as glass or plastic in the case of eyeglasses. Eyeglasses include those that, in addition to providing refractive correction, also provide protection of the eyes from sunlight (prescription sunglasses).

In order to provide vision correction, the surfaces of eyeglasses have a particular curvature, often designed specifically for the person who wears the corrective optics. It would be of value from the point of view of cost and weight to eliminate the need for surface curvature in wearable vision correction devices. Since diffractive waveplate lenses include surface layers sometimes only a few micrometers in thickness, compared to the few millimeters of thickness typical of common eyeglasses, creation of eyeglasses and other wearable optics for vision correction could be of significant value due to reduction in cost and weight.

In the case of swimming goggles and goggles designed for eye protection, the requirements of the primary application may conflict with the requirement for vision correction. For example, in the case of goggles designed to protect the eyes from small high-speed moving objects, the ballistic performance of the goggles is dependent on the cross section of the optical element covering the eye. It would be highly desirable in such applications as swimming goggles and goggles designed for eye protection to be able to provide vision correction by means of thin film layers, without having to disturb the underlying structure. Diffractive waveplate lenses have the capability to allow vision correction without changing the underlying optical element, simply by applying the diffractive waveplate lenses on the surface of each goggle.

Intraocular Lens Application

A common method of human vision correction is to insert an intraocular lens as a replacement for the biological lens of the eye. The most common reason for this replacement is to correct for the vision defects associated with cataracts. While the surgical techniques required to perform replacement of the biological lens with an artificial lens are highly developed and usually successful, the availability of an optical element that performs the same function, but in a lighter package, would provide an additional option for the refinement of this medical procedure. Since diffractive waveplate lenses, unlike conventional refractive lenses, can be very thin and yet still perform the desired function, a potentially valuable application of this technology is fabrication of such lenses, either alone or combined with other optical elements, as an intraocular replacement for the biological lens of the human eye.

Diffractive Waveplate Mirror

Figure 10:
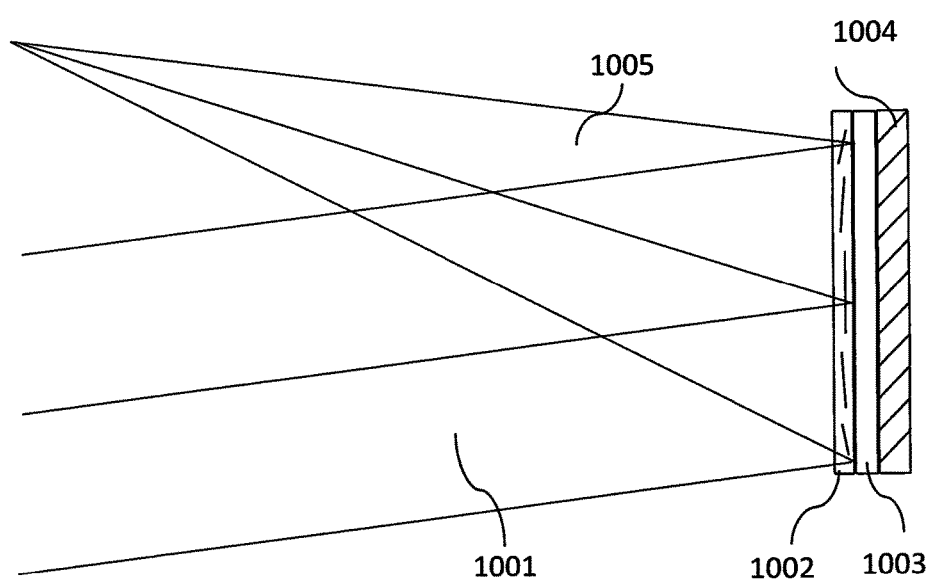
FIG. 10 shows a planar mirror converted into a focusing or defocusing mirror by addition of the diffractive waveplate lens coating.

While all of the exemplary embodiments discussed herein are of a realization of diffractive waveplate lenses employed in a mode in which the optical beam is transmitted through the thin film diffractive waveplate lens and through the underlying substrate, an alternative embodiment is to apply the thin film diffractive waveplate lens to a flat mirror as demonstrated in FIG. 10. In this manner, flat reflective optical elements can be fabricated to have a wide variety of beam deflecting properties, including the ability to focus light with a flat reflective optical element. In one of the preferred embodiments shown in FIG. 10, a flat mirror 1004 is coated with a quarter waveplate 1003 and a diffractive waveplate lens 1002. A circular polarized collimated light beam 1001 is thus reflected from the system a focused beam 1105, for example.

The exemplary embodiments described herein have assumed either explicitly or implicitly that the thin film constituting the diffractive waveplate lens is applied to the flat surface of a solid substrate such as glass. Neither the assumption of a solid substrate, nor the assumption of a flat surface, should be taken as restrictive in defining the potential embodiments of this invention. As will be evident to anyone skilled in the art, the coatings may be applied to curved substrates, and to flexible substrates. All of the exemplary embodiments described herein could also be realized with either a curved substrate, a flexible substrate, or a substrate that is both curved and flexible.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. An optical system with positive or negative focusing power for a circular polarized input beam, the system comprising:
    an optical substrate; and
    a diffractive waveplate lens with a flat front surface and a back surface adjacent to the optical substrate, one of the front surface and the back surface of the diffractive waveplate lens positioned to receive the circular polarized input optical beam to output defocused and focused beams from the circular polarized input beam; and
    a circular polarizer for providing selection of one of the defocused and the focused beams at the output of the diffractive waveplate lens, wherein the optical system is used for the positive or the negative focusing power for the circular polarized input beam.

2. The optical system as in claim 1 wherein components of said optical system are integrated onto the same substrate.

3. The optical system as in claim 1 wherein said optical substrate is a refractive lens and said diffractive waveplate is switchable between a diffractive state and a non-diffractive state.

4. The optical system as in claim 3 wherein said refractive lens is birefringent.

5. The optical system as in claim 1 wherein said optical substrate is a quarter waveplate film providing only one of focusing or defocusing for a linear polarized light propagated through the diffractive waveplate lens.

6. The optical system as in claim 1 wherein said substrate comprises:
a mirror and a quarter-wave retardation film.

7. The optical system as in claim 6 wherein said mirror and the quarter-wave retardation film are coatings on a flexible membrane.

\* \* \* \* \*